United States Patent [19]

Trick

[11] Patent Number: 4,928,706

[45] Date of Patent: May 29, 1990

[54] NOCTURNAL PENILE TUMESCENCE AND RIGIDITY MONITOR

[75] Inventor: Robert E. Trick, Racine, Wis.

[73] Assignee: Medical Engineering Corporation, Racine, Wis.

[21] Appl. No.: 200,041

[22] Filed: May 27, 1988

[51] Int. Cl.⁵ ............................................. A61B 5/10
[52] U.S. Cl. .................................... 128/774; 128/694; 33/512
[58] Field of Search .................. 128/774, 694; 33/512

[56] References Cited

U.S. PATENT DOCUMENTS

| | | | |
|---|---|---|---|
| 4,474,187 | 10/1984 | Timm et al. | 128/774 |
| 4,515,166 | 5/1985 | Timm | 128/774 |
| 4,572,211 | 2/1986 | Sagalowsky | 128/774 |
| 4,606,353 | 8/1986 | Timm | 128/774 |
| 4,747,415 | 5/1988 | Lavoisier | 128/774 |
| 4,766,909 | 8/1988 | Timm et al. | 128/774 |

OTHER PUBLICATIONS

Desai et al., Brit. J. of Urology, vol. 61, 1988, pp. 254-260.

Primary Examiner—Kyle L. Howell
Assistant Examiner—John C. Hanley
Attorney, Agent, or Firm—Rodman & Rodman

[57] ABSTRACT

The nocturnal penile tumescence and rigidity monitor includes a penile cuff formed on a nondistensible flexible membrane with an internal chamber defined therein. The chamber is initially filled with liquid from a reservoir until the cuff contacts the periphery of a flaccid penis. The flaccid penile diameter is correlated with the amount of liquid in the cuff by use of a weight sensor signal. During penile expansion, liquid in the cuff is displaced into the fluid reservoir and the tumescence is correlated with the amount of liquid displaced from the cuff by making a weight measurement of the reservoir after such liquid displacement. The weight sensor provides signals that permit a continuous plot of penile tumescence on a strip chart. When the penile tumescence is at a predetermined reference magnitude, a rigidity test is started. During rigidity testing, rigidity sensing probes on the cuff are displaced against the sides of the penis to measure the pressure of engagement which is correlated with penile rigidity. The rigidity test is repeated on a periodic basis as long as penile tumescence exceeds the predetermined reference magnitude. When the penile tumescence is less than the predetermined reference magnitude, the rigidity test is not performed.

19 Claims, 4 Drawing Sheets

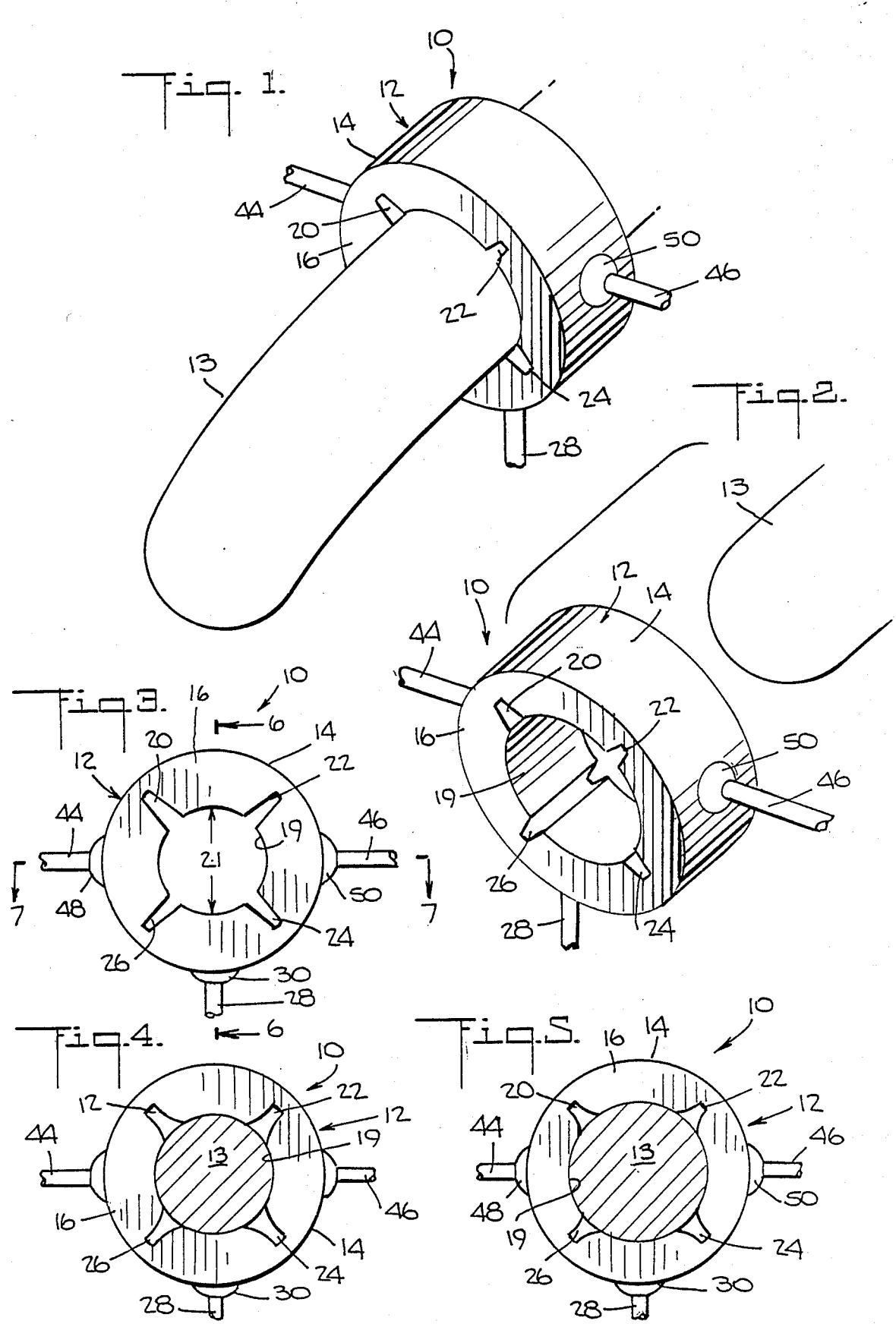

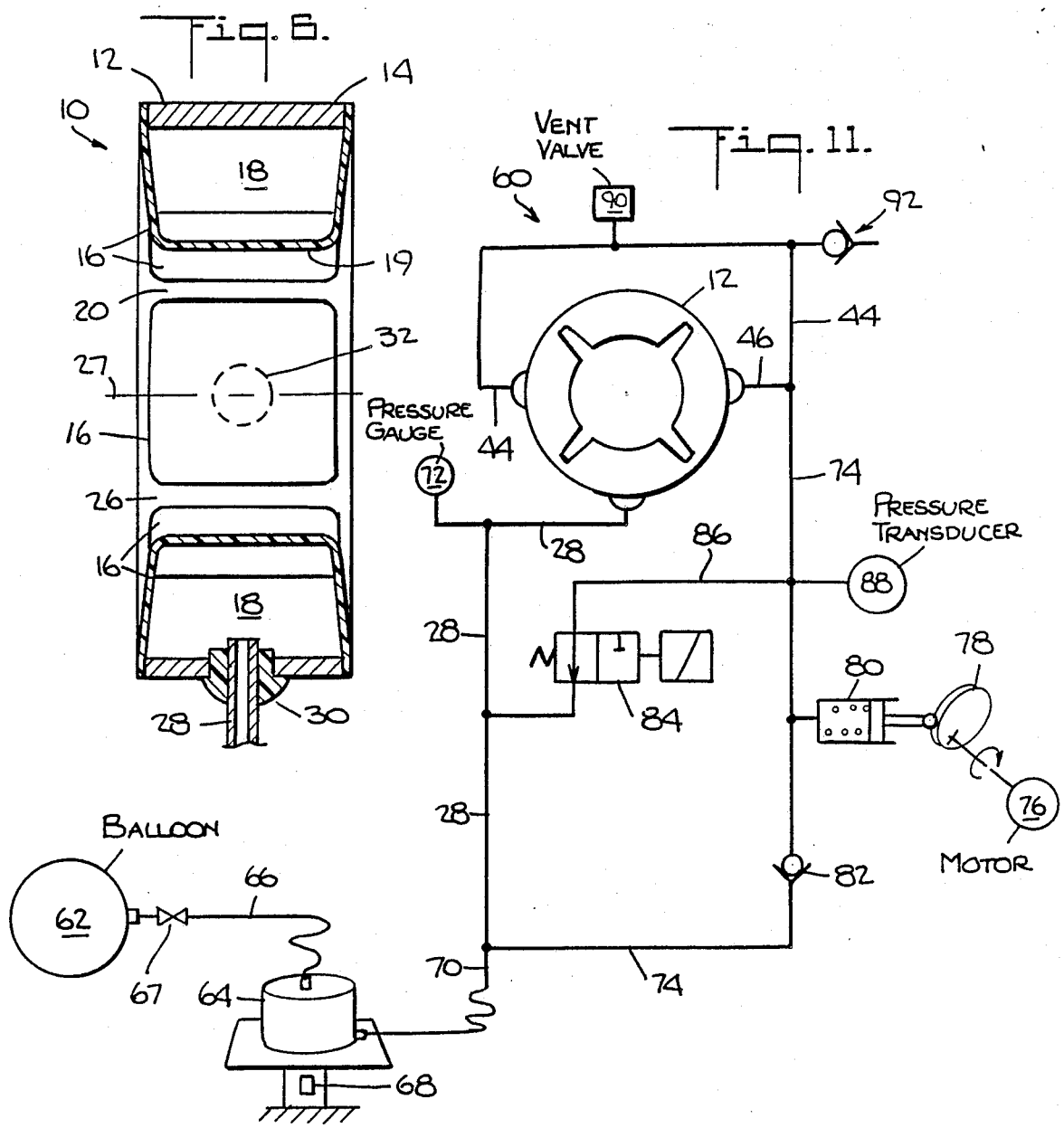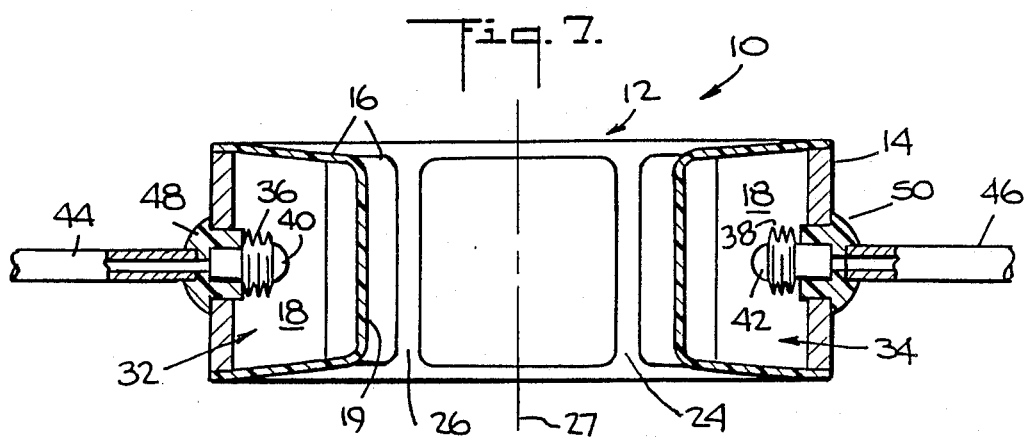

NOCTURNAL PENILE TUMESCENCE AND RIGIDITY MONITOR

BACKGROUND OF THE INVENTION

This invention is directed to nocturnal penile tumescence and rigidity monitoring systems and more particularly to a novel monitoring system incorporating a single penile sensor to sense penile tumescence and penile rigidity.

Studies of male impotence have shown that men with psychogenic impotence who have difficulty in attaining an erection while awake, generally have normal erections while sleeping. The studies also show that men with organic impotence, whether awake or asleep, are incapable of developing a normal erection. As a result of these studies, the monitoring of penile tumescence during nocturnal periods has become one of the bases for diagnosing sexual impotency.

If nocturnal penile tumescence monitoring indicates that impotency may be due to psychological factors, an appropriate therapy program can be developed. If such monitoring indicates organic impotency, therapy is usually ineffective, and a penile implant or other suitable prosthetic device may be necessary to assist in the development of an erectile condition. Thus, nocturnal penile tumescence monitoring is a reliable basis for determining whether therapy will be helpful or futile in correcting male impotency.

Some patients who undergo nocturnal penile tumescence evaluation are found to have significant penile expansion without the requisite rigidity that is needed to effect vaginal penetration. An assessment of penile rigidity as well as penile expansion is thus necessary for proper diagnosis of erectile impotence, and studies have shown that the most useful assessment of an erection is its rigidity characteristics.

The recognition that nocturnal penile conditions provide important data for diagnosing male erectile impotence has resulted in the development of various devices and techniques for monitoring penile tumescence and rigidity.

One known device for monitoring penile tumescence is disclosed in PCT Publication No. WO83/03748, wherein strain gauges are placed in two locations on the penis. The strain gauges include mercury tubing that is lengthened when the strain gauge is stretched, thereby increasing the electrical resistance. A readout of such electrical resistance is furnished to a recorder which records the data. This device measures penile tumescence only and provides no indication of rigidity.

Another known device for monitoring nocturnal penile tumescence and rigidity as disclosed in U.S. Pat. No. 4,515,166, employs a cable that forms a noose-like fitting around the penis. One end of the cable joins a sprocket assembly that drives a potentiometer. Changes in penile circumference are expected to affect the dimensions of the noose, causing the cable to move the sprocket assembly and drive the potentiometer to produce a corresponding electrical response. The disclosed cable and sprocket arrangement is relatively cumbersome to use and the mechanical play inherent in such device can lead to inaccurate data. Consequently there is a need to make frequent calibrations of the sprocket and drive assembly.

U.S. Pat. 4,515,166 also discloses a system for measuring penile rigidity that includes a torque motor on an elongated member that encircles the penis. The motor is activated at intervals to apply a force on the elongated member that is measured and correlated with rigidity. The use of cable displacement as a measure of compressibility or rigidity is a relatively cumbersome arrangement having mechanical play that is likely to result in inaccurate data.

It is thus desirable to provide a device for monitoring penile tumescence and rigidity which can be easily installed on a patient, is comfortable to use during nocturnal periods and provides accurate data relative to penile tumescence and rigidity.

OBJECTS AND SUMMARY OF THE INVENTION

Among the several objects of the invention may be noted the provision of a novel nocturnal penile tumescence and rigidity sensor, a novel nocturnal penile tumescence and rigidity sensor which displaces fluid as a basis for measuring penile tumescence, a novel nocturnal penile tumescence and rigidity sensor having rigidity sensing probes that are displaceable against the periphery of the penis to determine the rigidity thereof, a novel nocturnal penile tumescence and rigidity monitor which senses fluid displacement as a basis for measuring penile tumescence, and senses pressure as a basis for measuring penile rigidity, a novel nocturnal penile tumescence and rigidity monitor that uses a single penile cuff for providing data relating to penile tumescence and rigidity and a novel method of measuring penile tumescence and rigidity.

Other objects and features of the invention will be in part apparent and in part pointed out hereinafter.

The nocturnal penile tumescence and rigidity sensor, in accordance with the present invention, includes a penile cuff having a substantially rigid support shell and a flexible, nondistensible membrane adjoined to the shell to define a chamber within the cuff. Fluid inlet means for a fluid such as distilled water are joined to the shell portion for communication with the chamber. In addition, rigidity sensing means are joined to the shell and include a projection member that is projectible into the chamber. The projection member projects a predetermined amount and has a pressure sensing probe that engages the periphery of the penis when tumescence is at a predetermined magnitude. The pressure of engagement between the pressure sensing probe and the penis is measured to provide an analog signal that is characteristic of rigidity.

Tumescence is measured as a basis of fluid displacement from the chamber in the penile cuff. An initial predetermined amount of fluid is disposed in the cuff when the penis is in a flaccid condition. Expansion of the penis from the flaccid penile condition to a tumescent condition will cause movement of a measurable amount of liquid out of the chamber to provide an analog signal that is characteristic of tumescence.

The nocturnal penile tumescence and rigidity monitor which incorporates the penile tumescence and rigidity sensor includes a fluid reservoir and a low pressure pressurizing device for influencing movement of fluid from the reservoir into the cuff when the penis is in a flaccid condition. The fluid remaining in the reservoir after initial filling of the cuff chamber is weighed and the weight measurement is correlated with the flaccid penile diameter. As penile tumescence increases, fluid forced out of the cuff by penile expansion overcomes the predetermined low pressure that initially influenced fluid movement into the cuff.

At a predetermined penile tumescence that can be correlated with the erectile stage, the rigidity test is performed wherein the sensing probes are urged against the periphery of the penis. If the erectile stage is not reached the rigidity test is not performed.

Sensing devices for sensing the diameter of the penis and plotting such value on a graph are included within the monitoring system. Simultaneous recordation of penile rigidity and tumescence is provided when the required erectile stage is attained.

The nocturnal penile tumescence and rigidity monitor thus correlates a measurable amount of fluid with an initial flaccid penile diameter and further correlates fluid displacement from the cuff with developing tumescence. The monitor additionally correlates penile rigidity with the pressure of a sensing probe against the penis. Both functions are accomplished through use of a single penile cuff that operates as a tumescence and rigidity sensor.

The invention accordingly comprises the constructions and method hereinafter described, the scope of the invention being indicated in the claims.

DESCRIPTION OF THE DRAWINGS

In the accompanying drawings,

FIG. 1 is a simplified perspective view of a nocturnal penile tumescence and rigidity sensor in a monitoring position, for a nocturnal penile tumescence and rigidity monitor incorporating one embodiment of the invention;

FIG. 2 is a simplified perspective view thereof prior to placement in a monitoring position;

FIG. 3 is a front view thereof prior to placement in a monitoring position;

FIG. 4 is a front view thereof during monitoring, with the penis in the flaccid condition;

FIG. 5 is a front view thereof during monitoring, with the penis in an erectile condition;

FIG. 6 is a sectional view taken on the line 6—6 of FIG. 3;

FIG. 7 is a sectional view taken on the line 7—7 of FIG. 3;

FIG. 11 is a simplified schematic diagram of the nocturnal penile tumescence and rigidity monitor incorporating one embodiment of the invention;

Corresponding reference characters indicate corresponding parts throughout the several views of the drawings.

DETAILED DESCRIPTION OF THE INVENTION

Figure 8:
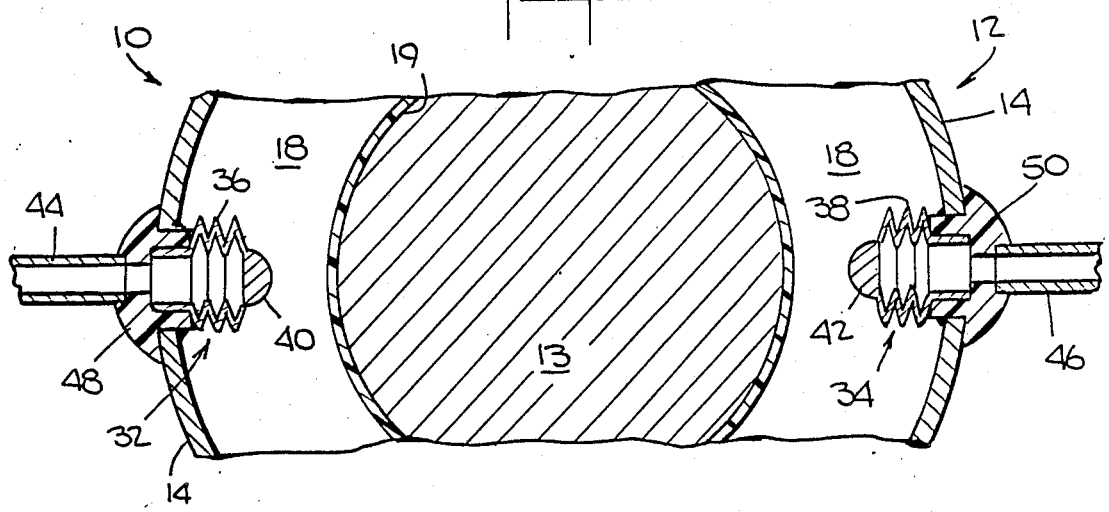
FIG. 8 is an enlarged fragmentary sectional view thereof during monitoring, with the penis in a flaccid condition.

A tumescence and rigidity sensor for a nocturnal penile tumescence and rigidity monitor incorporating one embodiment of the invention is generally indicated by the reference number 10 in FIG. 1.

The tumescence and rigidity sensor 10 includes a torus-shaped penile cuff 12 that can be slipped onto a flaccid penis 13. The penile cuff 12 has a rigid outer support shell 14 formed of a suitable plastic material such as Polysulfone. A nondistensible, flexible annular membrane 16, which can be formed of Polyurethane, is bonded or otherwise adjoined to the shell 14 thereby forming a substantially annular space or chamber 18 within the penile cuff 12, as shown most clearly in FIGS. 8–10.

The nondistensible membrane 16 also defines an inner circular wall 19 of the cuff 12 that has a normal inside diameter 21 (FIG. 3). The generally circular contour of the inner wall 19 is interrupted by a plurality of radial clearance spaces, such as 20, 22, 24 and 26. As used herein, the term "radial" is relative to a central axis 27 (FIGS. 6 and 7) of the cuff 12.

The tumescence and rigidity sensor 10 also includes a fluid inlet line or duct 28 having an end portion joined to the shell 14 with a leak-tight fitting 30. As most clearly shown in FIG. 6, the duct 28 communicates with the chamber 18 of the penile cuff 12.

Figure 9:
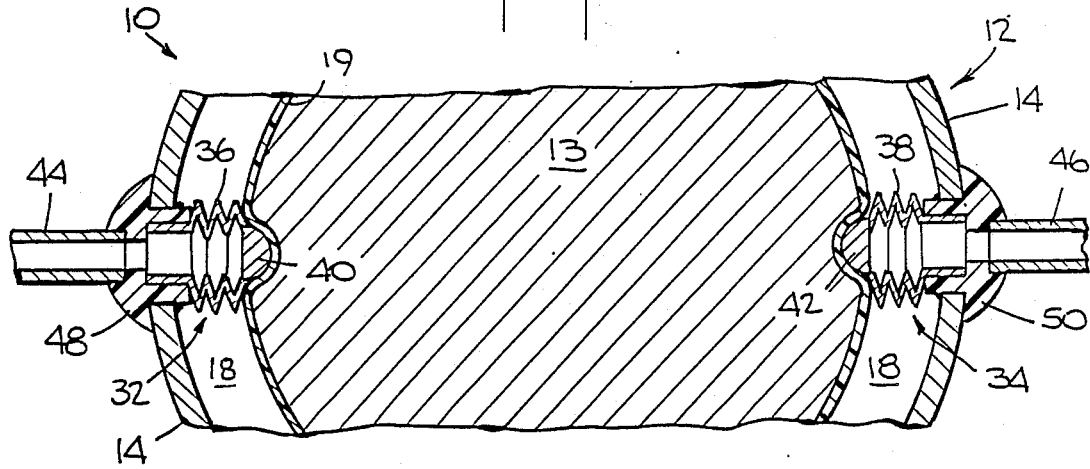
FIGS. 9 and 10 are enlarged fragmentary sectional views thereof during monitoring of penile rigidity.
Figure 10:
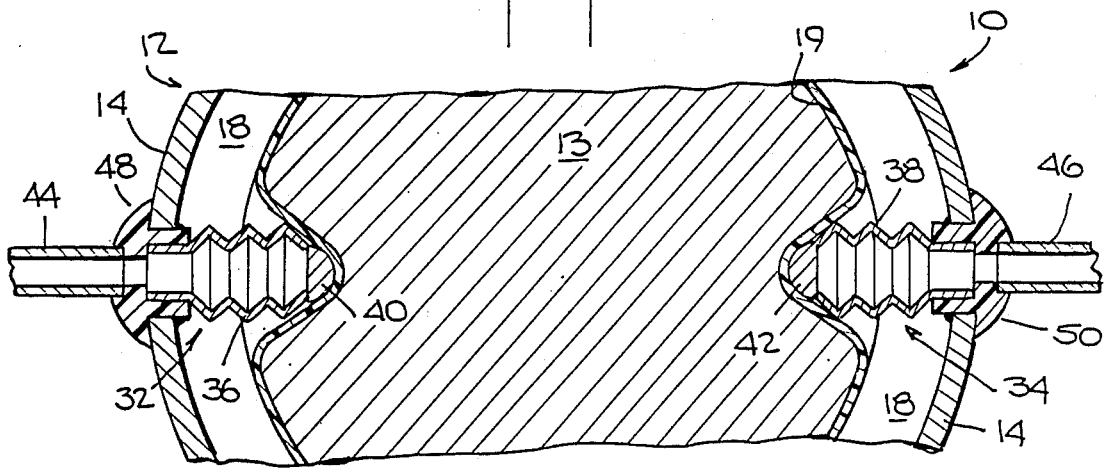

Referring to FIGS. 8–10, a pair of rigidity sensing members 32 and 34 are provided at opposite sides of the penile cuff 12, at the outer shell 14. The rigidity sensing members 32 and 34 include respective bellows members 36 and 38, the free ends of which are provided with respective sensing probes 40 and 42. The sensing probes 40 and 42 normally extend a predetermined distance into the annular space 18, free from contact with the inner annular wall 19 when the bellows members 36 and 38 are in a normally contracted condition as shown in FIG. 7.

Oppositely disposed duct members 44 and 46 communicate with the respective rigidity sensing members 32 and 34 through attachment fittings 48 and 50. The fittings 48 and 50 form a leak-tight joint between the respective sensing members 32,34, the duct members 44,46 and the shell 14.

The nocturnal penile tumescence and rigidity monitoring system which incorporates the tumescence and rigidity sensor 10 is generally indicated by the reference number 60 in FIG. 11. The system 60 includes any suitable low pressure supply, as for example, an air capacitance device such as a calibrated balloon 62, which furnishes a confined supply of air at a predetermined low pressure such as 30 cm (H$_2$O).

The balloon 62 communicates with a fluid reservoir or container 64 through a line 66 having a shut-off valve 67. The container 64 contains a predetermined amount of fluid such as distilled water (not shown), and is supported on a load cell 68 that senses the weight of fluid in the container 64. The load cell 68 provides an analog electrical signal of the weight of the container 64 to a logic circuit for controlling the operation of the system 60 as shown in schematic functional representation in FIG. 13.

The system 60 further includes a fluid supply line or duct 70 that joins the duct member 28 for feeding fluid into the chamber 18 of the penile cuff 12. If desired, a pressure gauge 72 can be provided on the line 28 for sensing pressure in the chamber 18. The fluid supply line 70 also joins a line 74 that communicates with the ducts 44 and 46.

A piston 80 that communicates with the line 74 is actuated by a cam 78 that is rotated by an electric motor 76. An anti-cavitation check valve 82 is provided on the line 74 between the piston 80 and the line 70. A two-way, electrically energized, directional valve 84 is connected across the lines 28 and 74 on a line 86. A pressure transducer 88 is connected to the line 74 between the two-way valve 84 and the line 46.

A vent valve 90 and anti-cavitating check valve 92 are provided intermediate the sensing members 32 and 34 on the duct or line 44.

In using the nocturnal penile tumescence and rigidity monitor 60, the penile cuff 12 is arranged around a flaccid penis 13 in the manner shown in FIG. 1. The cuff 12, when placed on the penis 13, should be oriented with the rigidity sensing members 32 and 34 along a horizontal axis substantially equidistant from the urethra (not shown). The cuff 12 is sized to loosely engage the flaccid penis 13 when the chamber 18 is in an initial empty state, free of liquid from the container 64.

While the fluid chamber 18 of the cuff 12 is empty, an initial weight measurement $W_1$ is obtained of the predetermined amount of fluid in the fluid container 64. It should be noted that the membrane 16 is collapsible toward the outer shell 14 when the chamber 18 is empty, thus providing a space for accommodation of the penis 13 that is larger than the inside diameter 21 of the cuff 12.

During the initial filling stage of the cuff 12, the shutoff valve 67 on the line 66 is opened to permit the low pressure air in the balloon 62 to influence movement of liquid, preferably distilled water, from the fluid container 64 into the fluid supply line 70. The water thus flows through the line 28 into the chamber 18 of the cuff 12 and through the line 74 into the lines 44 and 46 of the rigidity sensing members 32 and 34. The water can also flow from the line 28 through the two-way valve 84 on the line 86 to the line 74 and into the lines 44 and 46. The vent valve 90 vents off all trapped air in the rigidity monitor 60 to facilitate proper operation of the system.

The pressure imposed on the water by the balloon 62 is selected to be low enough to prevent expansion of the bellows members 36 and 38 during the initial filling stage of the cuff 12.

Water from the line 28 fills the chamber 18 until the inner annular wall 19 of the cuff 12 contacts the periphery of the flaccid penis 13. Water flow then ceases since the pressure from the balloon 62 on the water inside the chamber 18 of the cuff 12 is at a predetermined level that is insufficient to cause the cuff 12 to compress the flaccid penis 13. Thus when the cuff 12 fills sufficiently to engage the periphery of the penis 13, an equilibrium is reached between the pressure exerted by the penis 13 on the cuff 12 and the air pressure in the balloon 62.

Figure 12:
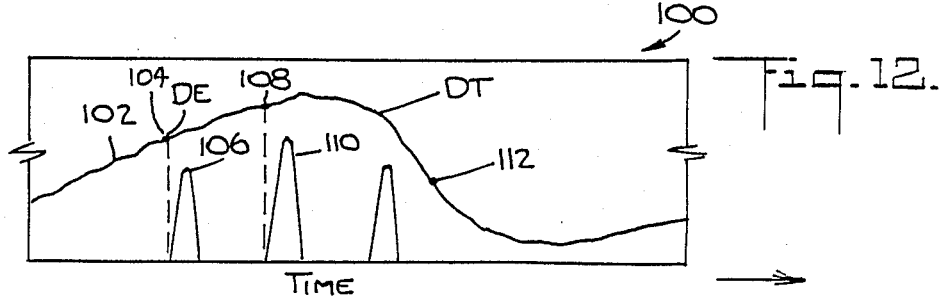
FIG. 12 is a graph of penile diameter and rigidity plotted against time.

At the described equilibrium point, a second weight measurement $W_2$ is obtained of fluid in the container 64. The difference in weight signals ($W_1-W_2$) from the sensor 68 is an analog of the diameter of the flaccid penis 13 (referred to as $D_f$). An initial readout of the flaccid penile diameter, expressed as $$D_f=(W_1-W_2)$$

can thus be plotted on a strip chart 100 as shown in FIG. 12 based on the difference in weight signals from the sensor 68, which measures the weight of fluid in the tank 64. The information relating to $D_f$ is stored in a logic circuit 120 shown in functional schematic form in FIG. 13. The storage of the flaccid penile diameter $D_f$ is generally indicated by the reference number 122.

A known flaccid penile diameter $D_f$ will generally expand a known amount $D_x$ (referred to as the add factor x) to reach the erectile stage (referred to as $D_e$), which can be expressed as $$D_e=D_f+D_x.$$

The penile magnitude $D_e$ which corresponds to the erectile condition is stored as a reference in the logic circuit 120. The storage function is generally indicated by the reference number 124 in FIG. 13. The reference penile magnitude $D_e$ is indicated by the reference number 104 in FIG. 12.

A continuous reading of penile tumescence (referred to as $D_t$) plotted against time is recorded as curve 102 on the strip chart 100. The rigidity monitoring function of the system 60 will not activate until the penile tumescence $D_t$ reaches the reference magnitude $D_e$, which is indicated at one instance on the penile tumescence graph 102 by the reference point 104. If the reference magnitude $D_e$ is never reached, the rigidity test will not be performed.

As penile tumescence $D_t$ increases to the reference value $D_e$, the penis 13 expands against the inner wall 19 of the cuff 12 compressing the chamber 18. Since the membrane 16 is nondistensible, the clearance spaces 20, 22, 24 and 26 take up any compression of the membrane 16 as shown by comparison of FIGS. 4 and 5.

Expansion of the penis 13 from the flaccid condition $D_f$ will thus cause fluid in the chamber 18 of the cuff 12 to flow back into the line 28 to accumulate in the fluid tank 64.

The flow back of fluid from the cuff 12 to the fluid tank 64, as tumescence increases from the flaccid condition $D_f$ is referred to as $W_{fb}$. Thus, a general expression for the increase in tumescence is $$D_t=D_f+W_{fb}$$

$$D_t=(W_1-W_2)+W_{fb}.$$

When penile tumescence increases from the flaccid condition $D_f$ to the reference erectile magnitude $D_e$ $$D_t=D_e$$

$$W_1-W_2+W_{fb}=D_f+D_x$$

$$W_1-W_2+W_{fb}=W_1-W_2+D_x$$

$$W_{fb}=D_x$$

The accumulation of fluid in the fluid tank 64 due to the flow back $W_{fb}$ from the chamber 18 of the cuff 12 is sensed by the sensor 68. The sensor 68 furnishes a signal to the logic circuit 120 corresponding to the displacement of fluid in the cuff 12, which is sensed as the total weight in the fluid tank 64 as a result of the flow back $W_{fb}$.

Thus, as penile tumescence $D_t$ increases from the flaccid condition $D_f$ to the erectile magnitude $D_e$, the volume of liquid in the cuff 12 decreases and the weight of liquid in the tank 64 increases.

When penile tumescence $D_t=$ the reference magnitude $D_e$, shown as the reference point 104 on the curve 102, the rigidity monitoring function of the nocturnal penile tumescence and rigidity system 60 becomes operative by a pre-programmed computer functionally represented in part, in the logic circuit 120, as the reference numbers 126 and 128.

During rigidity monitoring, the two-way valve 84 is shut off to prevent any fluid flow through the line 86. A timer, shown schematically as 128 in FIG. 12, periodically actuates the step motor 76 to rotate the cam 78 one revolution thereby stroking the piston 80. The piston 80 thus delivers a predetermined amount of fluid into the line 74 for delivery to the ducts 44 and 46. The pulsation of additional fluid from the piston 80 into the line 74 expands the bellows 36 and 38 a predetermined amount to project the sensing probes 40 and 42 against the periphery of the penis 13 as shown in FIG. 10.

The pressure on the sensing probes 40 and 42 is sensed by the pressure transducer 88 causing a signal to be processed and recorded on the strip chart 100 as a rigidity factor 106. It should be noted that the predetermined amount of fluid pulsed by the piston 80 into the line 74 is drawn back into the piston when the cam 78 completes its rotation cycle.

The rigidity monitoring test is conducted periodically at predetermined time intervals as long as the penile tumescence $D_t$ is at a magnitude which meets or exceeds that of the reference magnitude $D_e$ on the plot 102 of tumescence $D_t$. If, after a predetermined time interval the penile tumescence $D_t$ is at a magnitude such as 108, which exceeds the reference value $D_e$, the rigidity test will again be activated by the timer 128 to provide a rigidity factor reading 110 on the strip chart 100. The rigidity test recycling function is schematically indicated by the reference numbers 130 and 132 in FIG. 13.

Figure 13:
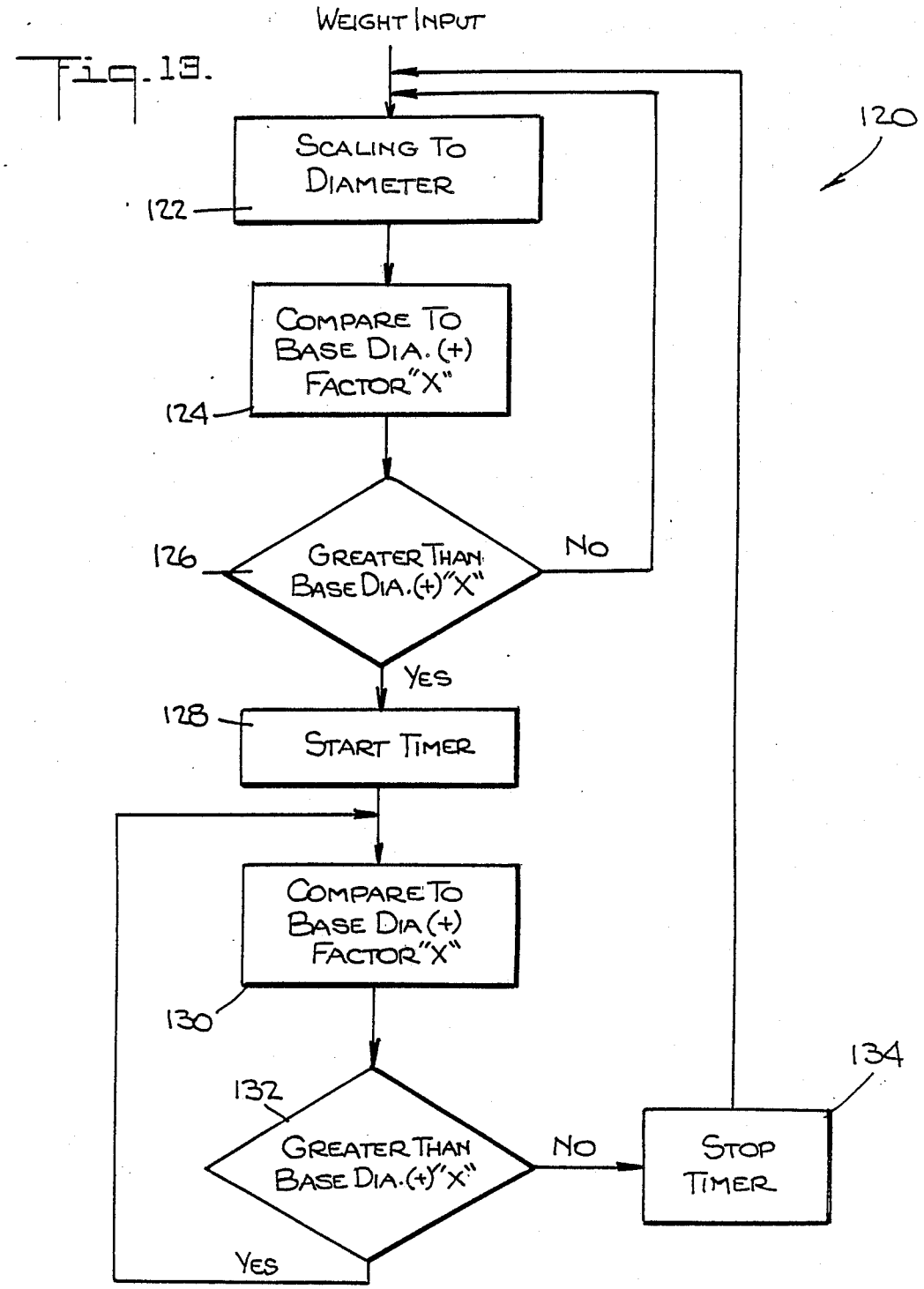
FIG. 13 is a simplified schematic functional diagram of the logic circuit and monitoring procedure for the nocturnal penile tumescence and rigidity monitor.

Once the weight signal from the weight load sensor 68 indicates that the penile tumescence $D_t$ is at a diametrical magnitude below the reference magnitude $D_e$, such as the penile diameter 112 in FIG. 12, the rigidity sensing function will not operate. The timer 128 will be stopped by a stop-timer function 134 (FIG. 13). However, the strip chart 100 will continue to provide a readout of the penile tumescence $D_t$ plotted against time based on the weight signals sensed by the weight sensor 68.

When the penile diameter decreases below the reference magnitude $D_e$ and the rigidity monitoring function is not activated, the two-way valve 84 opens to obviate any pressure buildup in the lines 44 and 46.

Upon completion of the nocturnal penile monitoring test, the balloon 62 is removed and pressure is thereby taken off of the system. This facilitates draining of water out of the system and back to the tank 64. The anti-cavitation check valve 92 introduces air to replace water as it is drained to the tank 64.

Thus the nocturnal penile tumescence and rigidity monitor provides a combination readout of penile tumescence $D_t$ and penile rigidity when tumescence reaches a predetermined reference magnitude $D_e$, the rigidity test function being inactive when the penile tumescence $D_t$ is of lesser magnitude than the reference magnitude $D_e$. The monitoring system thus provides a basis for future treatment of individuals by determining their capability of achieving an erectile condition and the rigidity characteristics associated with such erectile condition.

Some advantages of the present invention evident from the foregoing description include a nocturnal penile tumescence and rigidity monitor that operates on the basis of fluid displacement to measure penile tumescence and senses pressure as a basis for measuring penile rigidity. A further advantage is that a single penile sensor senses both tumescence and rigidity, is easy to install and functions in a relatively comfortable fashion to facilitate nocturnal testing. A further advantage is that the nocturnal penile tumescence monitor is easy to operate and adaptable for testing on individuals with diverse penile tumescence and rigidity characteristics.

In view of the above, it will be seen that the several objects of the invention are achieved and other advantageous results attained.

As various changes can be made in the above constructions and method without departing from the scope of the invention, it is intended that all matter contained in the above description or shown in the accompanying drawings shall be interpreted as illustrative and not in a limiting sense.

What is claimed is:

1. A nocturnal penile tumescence and rigidity sensor comprising,
   (a) a cuff member disposable on a penis, said cuff member having a substantially rigid support shell,
   (b) a flexible membrane adjoined to said shell portion to define a chamber within said cuff for holding fluid, said chamber being adapted to hold selected predetermined amounts of fluid respectively correlatable with a condition of penile flaccidity and a condition of penile tumescence to permit a detection of the conditions of penile flaccidity and penile tumescence,
   (c) fluid inlet and outlet means joined to said shell portion and communicable with said chamber to permit flow of said fluid into said chamber and out of said chamber in response to conditions of penile flaccidity and penile tumescence, and
   (d) rigidity sensing means joined to said shell and including projectable means in said chamber for projection against said penis through said membrane to enable the rigidity of said penis to be measured as a function of pressure data detected as a result of pressure between the projectable means and the penis.

2. The sensor as claimed in claim 1 wherein said cuff member is of toroidal shape.

3. The sensor as claimed in claim 2 wherein said cuff member has a central axis and said projectable means are moveable in a direction toward said central axis.

4. The sensor as claimed in claim 1 wherein said support shell is of annular shape, and said cuff member is of toroidal shape.

5. The sensor as claimed in claim 4 wherein said flexible membrane is nondistensible.

6. The sensor as claimed in claim 4 wherein said sensor has an inside surface defined by said flexible membrane and an outside surface defined by said shell portion, and wherein said inside surface is interrupted by a plurality of clearance spaces angularly spaced with respect to the center of said toroidal shape.

7. The sensor as claimed in claim 1 wherein said projectable means has a free end and a probe is provided at said free end for movement against said penis.

8. The sensor as claimed in claim 7 wherein said projectable means is expandable and contractible.

9. The sensor as claimed in claim 8 wherein said expandable and contractible projectable means includes means for reception of fluid, said expandable and contractible projectable means being normally contracted and actuated to expand by reception of a predetermined volume of said fluid.

10. The sensor as claimed in claim 9 wherein said expandable and contractible projectable means includes a bellows.

11. The sensor as claimed in claim 1 wherein said projectable means includes two probes oppositely disposed on said cuff for movement against corresponding opposite sides of said penis.

12. The sensor as claimed in claim 1 wherein said projectable means includes an expandable and contractible member with a free end and a probe at said free end.

13. The sensor as claimed in claim 1 wherein said fluid inlet means includes a single duct through which fluid enters and leaves said chamber.

14. A nocturnal penile tumescence and rigidity monitor comprising,
  (a) penile tumescence and rigidity sensor means disposable on a penis including a flexible nondistensible membrane and a chamber within said membrane,
  (b) reservoir means for holding a predetermined amount of fluid,
  (c) at least one fluid flow line connecting said reservoir means and said chamber,
  (d) pressurizing means for imposing a predetermined pressure on said reservoir fluid to cause said reservoir fluid to flow into said chamber,
  (e) said chamber holding a selected predetermined amount of fluid from said reservoir correlatable with penile tumescence,
  (f) sensing means for signaling the tumescent condition of said penis based on an analog of the selected predetermined amount of fluid in said chamber,
  (g) rigidity sensing means including at least one projectable member in said chamber projectable against said penis through said membrane to develop a pressure against said penis, and,
  (h) means for measuring the level of rigidity of said penis based on a correlation of pressure data detected as a result of pressure between the projectable member and the penis.

15. The monitor as claimed in claim 14 wherein a weight sensing means cooperates with said reservoir means to measure the weight of fluid in said reservoir means after the selected predetermined amount of fluid from said reservoir means is disposed in said chamber, to provide a weight signal that is correlatable with penile tumescence.

16. The monitor as claimed in claim 14 including means for pulsing said projectable member with a predetermined amount of liquid to project said projectable member against said penis to develop said pressure against said penis.

17. The monitor as claimed in claim 16 including means for sensing fluid pressure in said projectable member as a result of pressure between the projectable member and said penis, said sensing means including a pressure sensing transducer which senses the fluid pressure in said projectable member and provides a signal based on said pressure that is correlatable with the level of penile rigidity to permit a measurement of said penile rigidity.

18. A method of sensing penile tumescence comprising,
  (a) correlating penile tumescence with a volume or weight of liquid by
  (b) surrounding a flaccid penis with a flexible cuff having a chamber,
  (c) filling the chamber with a weight or volume of liquid corresponding to the flaccid penile diameter,
  (d) establishing an analog of the liquid in the chamber corresponding to the diameter of the flaccid penis,
  (e) establishing an analog of liquid that would be in the chamber corresponding to the diameter of a tumescent penis,
  (f) permitting the liquid to leave the chamber in response to a transition from flaccidity to tumescence and permitting liquid to enter the chamber in response to a transition from tumescence to flaccidity,
  (g) determining the weight or volume of liquid in the chamber and comparing the weight or volume with the analog of penile tumescence and penile flaccidity and determining tumescence from said step of comparing.

19. The method of claim 18 further including a method of measuring penile rigidity by establishing an analog of penile rigidity based on pressure data resulting from pressure between a projection member and the penis, the pressure data being developed by projecting the projection member against the penis and measuring the pressure data developed as a result of the pressure between the projection member and the penis for correlation with a level of penile rigidity.

* * * * *